US00PP19744P2

(12) United States Plant Patent
Heinrich

(10) Patent No.: US PP19,744 P2
(45) Date of Patent: Feb. 17, 2009

(54) ***CALIBRACHOA* PLANT NAMED 'WESCASTPI'**

(50) Latin Name: ***Calibrachoa* sp.**
Varietal Denomination: Wescastpi

(75) Inventor: Westhoff Heinrich, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 11/983,748

(22) Filed: Nov. 12, 2007

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Calibrachoa* plant named 'Wescastpi', characterized by its mounding and outwardly spreading to trailing growth habit; vigorous growth habit; relatively small leaves; numerous star-shaped dark and light red purple-colored flowers; and good garden performance.

1 Drawing Sheet

Botanical designation: *Calibrachoa sp.*
Cultivar denomination: 'Westcastpi'.

BACKGROUND OF THE INVENTION

The present invention relates to a new and distinct cultivar of *Calibrachoa,* botanically known as *Calibrachoa sp.* and hereinafter referred to by the name 'Wescastpi'.

The new *Calibrachoa* is a product of a planned breeding program conducted by the Inventor in Südlohn, Germany. The objective of the breeding program is to create new *Calibrachoa* cultivars with uniform plant habit and numerous attractive flowers.

The new *Calibrachoa* originated from a cross-pollination made by the Inventor in 2004 in Südlohn, Germany of a proprietary seedling selection of *Calibrachoa sp.* identified as code number 04P618, not patented, as the female, or seed, parent with a proprietary seedling selection of *Calibrachoa sp.* identified as code number 04P301, not patented, as the male, or pollen, parent. The new *Calibrachoa* was discovered and selected by the Inventor as a single flowering plant within the progeny of the stated cross-pollination in a controlled environment in Südlohn, Germany in 2005.

Asexual reproduction of the new *Calibrachoa* by vegetative cuttings in a controlled environment in Südlohn, Germany since 2005 has shown that the unique features of this new *Calibrachoa* are stable and reproduced true to type in successive generations.

SUMMARY OF THE INVENTION

The cultivar Wescastpi has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wescastpi'. These characteristics in combination distinguish 'Wescastpi' as a new and distinct cultivar of *Calibrachoa:*

1. Mounding and outwardly spreading to trailing growth habit.
2. Vigorous growth habit.
3. Relatively small leaves.
4. Numerous star-shaped dark and light red purple-colored flowers.
5. Good garden performance.

The new *Calibrachoa* can be compared to plants of the female parent selection. Plants of the new *Calibrachoa* differ from plants of the female parent selection in the following characteristics:

1. Plants of the new *Calibrachoa* have longer lateral branches than plants of the female parent selection.
2. Plants of the new *Calibrachoa* have smaller leaves than plants of the female parent selection.
3. Plants of the new *Calibrachoa* have larger flowers than plants of the female parent selection.
4. Plants of the new *Calibrachoa* and the female parent selection differ in flower color as plants of the female parent selection have red and yellow-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are shorter than plants of the male parent selection.
2. Plants of the new *Calibrachoa* have more flexible stems than plants of the male parent selection.
3. Plants of the new *Calibrachoa* have smaller leaves than plants of the male parent selection.
4. Plants of the new *Calibrachoa* have larger flowers than plants of the male parent selection.
5. Plants of the new *Calibrachoa* and the male parent selection differ in flower shape as plants of the male parent have more rounded flowers.

Plants of the new *Calibrachoa* can be compared to plants of the cultivar Cal Corink, disclosed in U.S. Plant Pat. No. 17,304. In side-by-side comparisons conducted in Südlohn, Germany, plants of the new *Calibrachoa* differed from plants of the cultivar Cal Corink in the following characteristics:

1. Plants of the new *Calibrachoa* were more upright than and not as trailing as plants of the cultivar Cal Corink.
2. Plants of the new *Calibrachoa* had shorter lateral branches than plants of the cultivar Cal Corink.
3. Plants of the new *Calibrachoa* had smaller leaves than plants of the cultivar Cal Corink.
4. Plants of the new *Calibrachoa* had larger flowers than plants of the cultivar Cal Corink.
5. Plants of the new *Calibrachoa* and the cultivar Cal Corink differed in flower color as plants of the cultivar Cal Corink had coral pink-colored flowers with red markings.

BRIEF DESCRIPTION OF THE PHOTOGRAPH

The accompanying colored photograph illustrates the overall appearance of the new *Calibrachoa,* showing the colors as true as it is reasonably possible to obtain in colored reproductions of this type. Colors in the photograph may differ slightly from the color values cited in the detailed botanical description which accurately describe the colors of the new *Calibrachoa.* The photograph comprises a side perspective view of a typical flowering plant of 'Wescastpi' grown in a hanging basket container.

DETAILED BOTANICAL DESCRIPTION

The aforementioned photograph and following observations, measurements and values describe plants grown in Südlohn, Germany, under commercial practice during the summer in a glass-covered greenhouse with day temperatures ranging from 20° C. to 25° C., night temperatures ranging from 16° C. to 18° C. and light levels ranging from 3,000 lux to 50,000 lux. Rooted young plants were grown for about 25 weeks when the photograph and description were taken. In the following description, color references are made to The Royal Horticultural Society Colour Chart, 2001 Edition, except where general terms of ordinary dictionary significance are used.

Botanical classification: *Calibrachoa sp.* cultivar Wescastpi.

Parentage:

*Female, or seed, parent.*—Proprietary seedling selection of *Calibrachoa sp.* identified as code number 04P618, not patented.

*Male, or pollen, parent.*—Proprietary seedling selection of *Calibrachoa sp.* identified as code number 04P301, not patented.

Propagation:

*Type.*—By vegetative cuttings.

*Time to initiate roots, summer.*—About 10 to 14 days at temperatures of 20° C.

*Time to initiate roots, winter.*—About 16 to 18 days at temperatures of 20° C.

*Time to produce a rooted young plant, summer.*—About 21 to 24 days at temperatures of 20° C.

*Time to produce a rooted young plant, winter.*—About 24 to 26 days at temperatures of 20° C.

*Root description.*—Fibrous, fine; color, close to 155A.

*Rooting habit.*—Freely branching; moderately dense to dense.

Plant description:

*Plant and growth habit.*—Mounding and outwardly spreading to trailing plant habit; plants roughly spherical in shape. Freely branching habit with lateral branches potentially developing at every node. Vigorous growth habit.

*Plant height.*—About 14 cm.

*Plant diameter.*—About 40 cm.

Lateral branch description:

*Length.*—About 40 cm.

*Diameter.*—About 2.5 mm to 3.2 mm.

*Internode length.*—About 1.2 cm.

*Strength.*—Strong; flexible.

*Aspect.*—Initially upright to outwardly spreading to trailing.

*Texture.*—Pubescent.

*Color.*—146B.

Foliage description:

*Arrangement.*—Alternate, simple; sessile.

*Length.*—About 3.2 cm.

*Width.*—About 8 mm.

*Shape.*—Narrowly elliptic.

*Apex.*—Obtuse to slightly acute.

*Base.*—Attenuate.

*Margin.*—Entire.

*Texture, upper and lower surfaces.*—Pubescent.

*Venation pattern.*—Pinnate; arcuate.

*Color.*—Developing foliage, upper surface: 146A. Developing foliage, lower surface: 146B. Fully expanded foliage, upper surface: 147A; venation, slightly lighter than 147A. Fully expanded foliage, lower surface: 147B; venation, slightly lighter than 147B.

Flower description:

*Flower arrangement and habit.*—Single salverform flowers arranged singly arising from leaf axils. Freely flowering habit with usually about seven to nine flowers and flower buds per lateral branch. Flowers not persistent. Flowers face mostly outwardly.

*Fragrance.*—None detected.

*Natural flowering season.*—Plants of the new *Calibrachoa* initiate and develop flowers about 13 to 14 weeks after planting. Plants flower continuously from April to October in Germany.

*Flower longevity.*—Individual flowers last about five to seven days on the plant.

*Flower diameter.*—About 3.4 cm.

*Flower length (height).*—About 2.8 cm.

*Flower throat diameter.*—About 6.7 mm.

*Flower tube diameter, base.*—About 2.75 mm.

*Flower tube length.*—About 1.5 cm.

*Flower bud.*—Shape: Elongated oblong. Length: About 2.2 cm. Diameter: About 3.9 mm. Color: 144D, venation, 166A; towards the apex, 182D.

*Corolla.*—Arrangement: Five petals fused at the base and opening into a flared trumpet; flowers star-shaped. Petal length from throat: About 1.6 cm. Petal lobe width: About 1.5 cm. Petal shape: Roughly obovate. Petal apex: Cuspidate. Petal margin: Entire. Petal texture, upper and lower surfaces: Smooth, glabrous; satiny. Color: Petal, when opening, upper surface: Center, 61A to 61B; towards the margins, 61B to 61C; at the margins, 62B. Petal, when opening, lower surface: 63A to 63C. Petal, fully opened, upper surface: Center, 67A; towards the margins, N66A; at the margins, 68B; midvein, N79A; lateral veins, 59A. With development, color becoming closer to N74A to N74B at the center; towards the margins, N74B; at the margins, N74D. Petal, fully opened, lower surface: 68B to 68D; venation, 166A. With development, color becoming closer to 75A to 75C. Throat: 9B; venation, 166A. Tube: 4C; venation, 166A.

*Calyx.*—Arrangement: One star-shaped calyx tube with five sepals fused at the base per flower. Sepal length: About 1.6 cm. Sepal width: About 3.6 mm. Sepal shape: Lanceolate. Sepal apex: Acute. Sepal margin: Entire. Sepal texture, upper and lower surfaces: Pubescent. Color, upper and lower surfaces: 137A to 137C.

*Peduncles.*—Length: About 1.85 cm. Diameter: About 0.95 mm. Strength: Moderately strong; flexible, Texture: Densely pubescent. Color: Between 146A and 144A.

*Reproductive organs.*—Stamens: Quantity/arrangement: About five per flower. Filament length: About 1 cm. Filament color: 144D. Anther shape: Reniform, two-parted. Anther length: About 1.2 mm. Anther diameter: About 1.5 mm. Anther color: 5A. Pollen amount: Moderate. Pollen color: 5A. Pistils: Quantity: One per flower. Pistil length: About 1.1 cm. Style length: About 7.3 mm. Style color: 144C. Stigma shape: Ovate. Stigma color: Between 146A and 144A. Ovary color: 144C flushed with close to 187A. Seeds: Seed development has not been observed on plants of the new *Calibrachoa.*

Garden performance: Plants of the new *Calibrachoa* have been observed to have good garden performance and tolerate wind, rain and temperatures ranging from about 5° C. to about 30° C.

Pathogen/pest resistance: Plants of the new *Calibrachoa* have not been observed to be resistant to pathogens and pests common to *Calibrachoa.*

It is claimed:

1. A new and distinct *Calibrachoa* plant named 'Wescastpi' as illustrated and described.

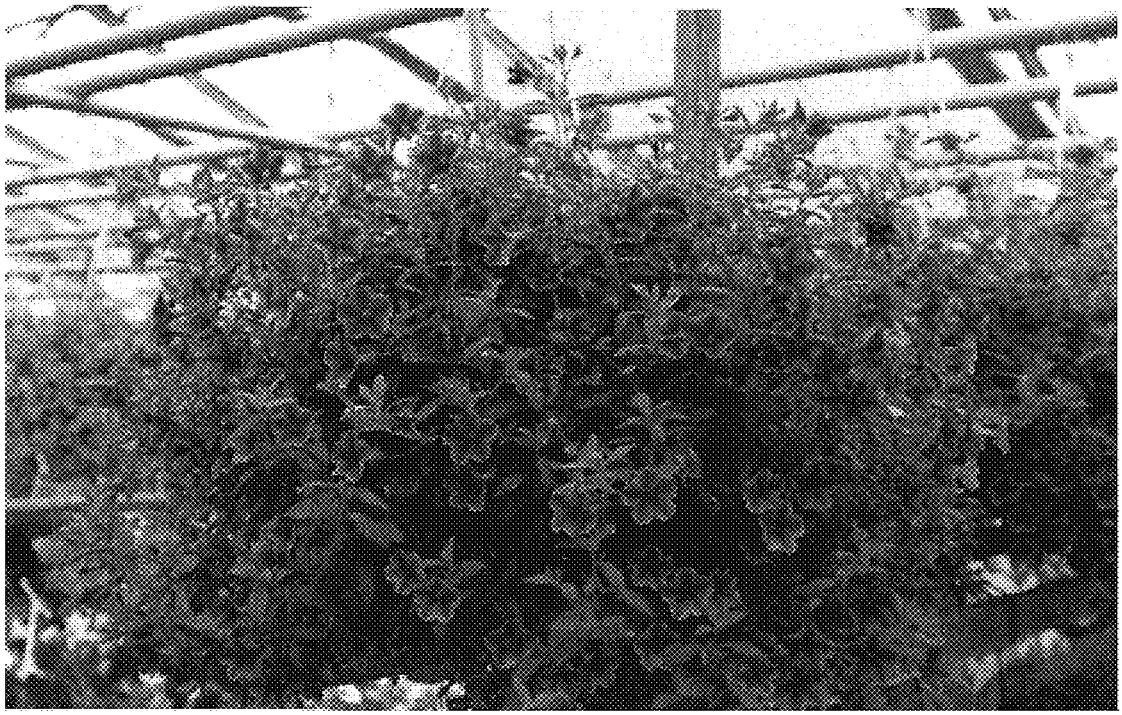

* * * * *